United States Patent [19]

Borodkin

[11] 3,947,572

[45] Mar. 30, 1976

[54] IRON-RESIN ADSORBATE

[75] Inventor: Saul Borodkin, Village of Libertyville, Ill.

[73] Assignee: Abbott Laboratories, North Chicago, Ill.

[22] Filed: July 1, 1974

[21] Appl. No.: 484,387

[52] U.S. Cl. ............................. 424/79; 260/2.2 R
[51] Int. Cl.² .... A61K 31/74; C08J 3/12; C08J 5/20
[58] Field of Search ..................... 424/79; 260/2.2 R

[56] References Cited
UNITED STATES PATENTS

| | | | |
|---|---|---|---|
| 3,012,937 | 12/1961 | Schlechting | 424/79 |
| 3,143,465 | 8/1964 | Keating | 424/79 |
| 3,665,073 | 5/1972 | Marshall et al. | 424/79 |

Primary Examiner—Donald B. Moyer
Attorney, Agent, or Firm—Paul D. Burgauer; Robert L. Niblack

[57] ABSTRACT

This invention is directed to a powder suitable for the preparation of a hematinic suspension which provides for controlled release of the iron contained in said powder. The powder to which this invention refers consists essentially of particles below a diameter of 50 microns. It is an iron adsorbate containing a specified amount of ferrous ions adsorbed on a specified cation exchange resin.

3 Claims, No Drawings

IRON-RESIN ADSORBATE

DETAILED DESCRIPTION OF THE INVENTION

Hematinics have been used in therapy for many years. Historically, iron preparations always represented the most convenient and cheapest form of a hematinic, although a number of well known disadvantages are connected with their use. Among those disadvantages are, depending on the form of the iron salt, the gastric irritation, the objectionable taste, the unpleasant mouth feel, staining of teeth, and the lack of stability of the ferrous salts.

In order to overcome some of these disadvantages, iron salts have in the past been combined with resins or they have been coated with resinous materials in order to provide passage through the upper G.I. tract without substantial exposure of the iron salt. Unfortunately, this results in a more or less uncontrollable release of the iron from such preparations, a release which begins only after a time period which depends on the size or thickness of the coating or, the iron is only released in the intestinal tract by virtue of an acid resistant coating preventing exposure of the active iron ion in the stomach. Also, coated particles of this type are ordinarily unsuitable for liquid preparations since part of the coating may dissolve in the storage bottle, exposing the iron salt.

It is therefore an object of the present invention to provide a hematinic which produces prompt and controlled release of iron. It is another object of this invention to provide a hematinic suitable to be administered in an easily and readily preparable suspension. It is still a further object of this invention to provide a hematinic of acceptable taste, mouth feel, high stability and suitable for preparing a suspension which essentially does not stain teeth.

These and other objects are accomplished by providing a powder suitable for the preparation of a palatable oral dosage form for a controlled release hematinic consisting essentially of an iron adsorbate containing between 5 and 12% by weight of ferrous ions adsorbed on a nuclear sulfonic cation exchange resinous copolymer of styrene and divinylbenzene containing between 1 and 16% by weight of said divinylbenzene, said powder being essentially free of particles with a diameter of above 50 microns.

In a simple embodiment, the suitable resin selected for the above purpose is converted into its hydrogen cycle, washed thoroughly with deionized water and a solution of ferrous sulfate is passed through said resin. The excess liquid is drained from the adsorbate so formed and the latter is dried, preferably without exposure to air, at 50°–90° C., over a period of several hours or days.

A particularly suitable resin for the above purpose is the polystyrene type sulfonic acid ion exchange resin containing about 8% divinylbenzene in cross-linkages and having a particle size range of 20 – 50 mesh. Resins of this type are commercially available as Amberlite IR-120, DOWEX 50-X8, Zeocarb 225, etc. The use of such a resin allows the ferrous sulfate solution to be adsorbed in a column operation, i.e., almost instantaneous adsorption is obtained. It was found that the degree of cross-linkage between 1 and 16% had little effect on drug release from the resin, but it was noted that adsorption of the iron sulfate was somewhat slower with resins containing 12% (e.g., Amberlite IR-124) or 16% (e.g., Biorad AG 50 W-X16) of divinylbenzene.

It was also observed that adsorption of the iron ions unto a polysulfonic acid resin with smaller particle size ranges was more difficult by column operation and with particles passing a 200 mesh sieve, adsorbing the iron salt by the above column operation must be replaced by a batch operation which yields lower potency. Thus, in order to obtain a resin absorbate containing substantially no particles with a diameter of above 50 microns, best results are attained by adsorbing the iron salt on resin particles not passing a 100 mesh sieve or larger using a resin column operation and to follow this adsorption by milling the dried adsorbate to the necessary mesh size.

In a preferred embodiment, a sulfonic cation exchange resin of the polystyrene type cross-linked with 1 – 16% of divinylbenzene and particle size range of 20 – 50 mesh in the hydrogen cycle is charged with a ferrous sulfate solution containing 1 equivalent of iron per equivalent resin exchange capacity. Upon draining and vacuum drying, the resin shows to contain 96 – 98% of the ferrous ions added or 105 – 120 mg. of ferrous ion per gram adsorbate. When this procedure is replaced by a batch operation, it was observed that a 30 – 50% excess of ferrous sulfate was necessary to attain an adsorbate potency of 90 – 100 mg./g. of adsorbate.

While it is possible to make adsorbate particles of the required mesh size from resin particles of suitable size (substantially no particles of above 50 microns diameter) through batch operation, the preferred method to attain the desired particles is by column adsorption in the above manner and milling the powder obtained after drying. This milling can be done by the so-called dry milling process using the fluid energy mill or by wet-ball milling using a suitable medium such as water or sorbitol solution.

The desired final adsorbate particles, i.e., the above powder obtained after drying the milled resin adsorbate of suitable particle size, can easily be placed in a stable suspension. In a general embodiment, 50 – 250 parts (all parts are by weight) together with 15 to 25 parts of the suspending agent are suspended in 50 parts of glycerine containing the desired sweetening and/or flavoring agents. The pH is adjusted to 3.0 and the volume is adjusted to 1000 parts with a suitable, nontoxic, preferably physiologically inert vehicle. Among the suitable vehicles are a 70% aqueous sorbitol solution, an aqueous glucose solution or the like.

Among the suspending agents, water-soluble or water-dispersible polymers are desirable, many of those are well known in the trade, e.g., hydroxypropylmethylcellulose, sodium carboxymethylcellulose, magnesium aluminum silicate, xanthan gum or certain other polysaccharide gums and the like. It may also be desired to add thickening agents to the suspension which helps to minimize the adhesion of adsorbate particles to parts of the buccal cavity. Formulated suspensions of this type containing 52.5 – 105 milligrams of ferrous iron per 5 ml. suspension show no detectable oxidation to ferric iron after 2 months at 25°, 40° and 50° C. By the addition of a stabilizer such as ascorbic acid, even longer shelf life can be attained.

In order to illustrate the process for making the particles of the present invention, reference is made to the following example which also shows a final product made from the particles of the invention and its physiological effect. However, this example is not intended to limit the invention in any respect.

EXAMPLE

In a suitable tank, 32.4 kg. of Amberlite IR-120 was agitated for 30 minutes with 50 – 60 liters of deionized water. This mixture was filled into a glass column of 6 inch diameter and 15 feet height, containing 5 liters of deionized water. The excess water was drained but leaving the resin bed surface below the water surface level. Another 60 liters of deionized water was pressed into the column from the bottom at a rate to increase the resin bed volume by about 30 – 50%. The resin was transferred to its hydrogen cycle in known fashion using the bottom inlet for the dilute hydrochloric acid solution. The resin in the hydrogen form is then again washed with deionized water.

A solution of 17.8 kg. of ferrous sulfate in 340 liters of distilled water containing 270 g. of ascorbic acid was then passed upwards through the column at a rate of 40 liters per hour. The column was then washed with 20 liters of distilled water, the water was drained and the resin was placed on trays and vacuum dried at 70° C. for 48 hours to yield 25 kg. of adsorbate particles containing 10.8% ferrous ions, less than 0.5% of moisture and no ascorbic acid (demonstrated by qualitative UV scan). The total iron content of the adsorbate is 11%.

The above iron-Amberlite adsorbate (3.5 kg.) was milled through a 0.010 inch herringbone slot screen on the Microsample mill at about 13000 rpm, using dry ice during milling. The milled adsorbate was placed in a plastic bag and gassed with dry nitrogen until it warmed up to the point when condensation of moisture did not occur. This was done to minimize moisture pick-up.

The iron adsorbate (3.4 kg.), 7.5 g. of a preservative mixture (methylparaben and propylparaben 10:1), 102 g. of ascorbic acid and 10.2 kg. of a 70% aqueous sorbitol solution containing 6.8 g. of a xanthan gum were placed in a ball mill and milled for eight hours under a nitrogen atmosphere. The "preslurry" obtained in this manner is suitable as a concentrate stock solution which is stable over extended periods of time under ordinary storage conditions.

In order to make a hematinic suspension suitable for oral administration, 125 ml. of glycerine and 100 ml. of water are heated and 2 g. of methylparaben and propylparaben (9:1) are added and mixed in for complete solution. To this solution is added 340 g. of a 70% aqueous sorbitol solution and after mixing, 3.5 g. of xanthan gum is mixed in at a temperature of 60° – 70° C. for 1/2 hour. At the same temperature, 2 g. of saccharin and 100 g. of sugar are mixed into the solution at 60° – 70° C., the solution is then cooled to 25° C. while bubbling nitrogen gas therethrough. Nitrogen bubbling is continued throughout the rest of the operation which comprises adding 105 g. of the above "premix", mixing for ½ hour, adding 100 g. of 35% ascorbic acid, mixing, adding 1 ml. of D & C Red No. 19 Dye in slightly warmed purified water, adding 2 ml. of flavoring components ordinarily used in such applications, and adjusting the pH with a 20% aqueous sodium hydroxide solution to 2.8 – 3.0. Purified water is then added to make up a total volume of 1 liter and the mixture is well stirred under vacuum to a constant volume and until uniform.

Two groups of five healthy adult subjects each were used in studies of serum iron levels after being given an oral dose of the above final suspension representing 105 mg. of elemental iron in the form of the desired adsorbate. One of the groups was fasted for 12 hours prior to the administration of the iron adsorbate with breakfast served one hour after dosing. The other group received breakfast one-half hour before dosing. Blood samples were taken before dosing and at 1, 2, 4, 6 and 8 hours after dosing and were assayed for serum iron, using an automated method.

In the fasting group, the serum iron concentration before dosing showed a mean value of 1.56 mcg./ml.; after one hour this value was 1.98, at 2 hours it was 2.69, at 4 hours it was 2.41, at 6 hours it was 2.31 and at 8 hours it was 1.62 mcg./ml. with an individual peak level average of 2.74 mcg./ml. In the nonfasting group, the mean value at the beginning was 1.30; after one hour it was 1.48, after 2 hours it was 1.60, after 4 hours it was 1.68, after 6 hours it was 1.38 and after 8 hours it was 1.32 mcg./ml. with an individual peak level average of 1.85 mcg./ml.

At each sampling time the mean serum levels were much higher for the fasting subjects. Part of this difference was due to hemolysis in several of the fasting blood samples compared to only one hemolyzed nonfasting blood sample. However, the blood samples without hemolysis under the fasting conditions were generally higher than the corresponding nonfasting samples.

In another blood level study carried out with ten human volunteers and a 105 mg. iron dosage given orally in the form of the above suspension, it showed that blood serum iron levels were the same as those obtained by administering capsules containing ferrous sulfate.

One of the major advantages of the suspension made from the particles of the present invention is the fact that the release of ferrous ions is controlled. This means that any given time after oral ingestion of a therapeutic iron dose of this suspension, no more than about 25% of said iron dissolves in the fluid of the stomach. In turn, this means that gastrointestinal side effects, i.e., nausea, diarrhea and intestinal colic, are minimized and that the equilibrium that results from dissolving parts of the iron present per time increment provides a means for providing a desirable level of iron with less frequent dosing. Also, the suspension can be formulated in such a way that never more than about 2 – 4% of the iron of the adsorbate is in the solution. This is done by keeping the cation concentration of the suspension low, for instance, as exemplified above. In turn this means that staining of teeth and the "iron" taste of the suspension is minimized. Furthermore, the particle size in the suspension is such that the unpleasant mouth feel often encountered with known iron preparations is largely absent. Although taste masking with well accepted flavoring agents will further improve the acceptability of the above suspension, only minimal effort is required in this direction by suspending the particles of this invention. Also, due to the controlled release resulting from suspending the particles of this invention, amounts of iron can be administered that are 2 – 4 times greater than possible by using more conventional dosage means due to gastrointestinal disorders caused by such conventional hematinics.

What is claimed is:

1. In a powder suitable for the preparation of a palatable oral dosage form for a hematinic suspension for controlled release of the iron contained therein in the form of an iron adsorbate consisting essentially of 5-12% by weight of ferrous ions adsorbed on a nuclear sulfonic cation exchange resinous copolymer of styrene and divinylbenzene containing between 1% and 16% by weight of said divinylbenzene, the improvement being that essentially all iron adsorbate particles have a diameter below 50 microns.

2. The powder of claim 1 wherein said adsorbate contains 10 – 12% by weight of ferrous ions.

3. The powder of claim 1 suspended in a liquid pharmaceutical carrier suitable for oral administration, said powder being present in an amount of from 5 – 25 parts by weight per 100 volume parts.

* * * * *